United States Patent
Suzuki et al.

(10) Patent No.: US 10,779,729 B2
(45) Date of Patent: Sep. 22, 2020

(54) OPHTHALMIC APPARATUS

(71) Applicant: NIDEK CO., LTD., Gamagori, Aichi (JP)

(72) Inventors: Keita Suzuki, Gamagori (JP); Yoshihiko Sugimoto, Gamagori (JP)

(73) Assignee: NIDEK CO., LTD., Gamagori (JP)

( * ) Notice: Subject to any disclaimer, the term of this patent is extended or adjusted under 35 U.S.C. 154(b) by 307 days.

(21) Appl. No.: 15/830,409

(22) Filed: Dec. 4, 2017

(65) Prior Publication Data

US 2018/0153403 A1 Jun. 7, 2018

(30) Foreign Application Priority Data

Dec. 5, 2016 (JP) .................. 2016-235510
Dec. 5, 2016 (JP) .................. 2016-235511
Sep. 28, 2017 (JP) .................. 2017-187997

(51) Int. Cl.
*A61B 3/10* (2006.01)
*A61B 3/15* (2006.01)
*A61B 3/117* (2006.01)
*A61B 3/00* (2006.01)

(52) U.S. Cl.
CPC ............. *A61B 3/15* (2013.01); *A61B 3/0075* (2013.01); *A61B 3/117* (2013.01); *A61B 3/0008* (2013.01)

(58) Field of Classification Search
CPC ....... A61B 3/0075; A61B 3/0083; A61B 3/12; A61B 3/145; A61B 3/152; A61B 3/15; A61B 3/117; A61B 3/0008
USPC .................................................. 351/208
See application file for complete search history.

(56) References Cited

U.S. PATENT DOCUMENTS

| | | | |
|---|---|---|---|
| 8,967,810 B1 | 3/2015 | Prager et al. | |
| 2015/0092160 A1 | 4/2015 | Chen et al. | |
| 2018/0078129 A1* | 3/2018 | Vadakke Matham .... | A61B 3/00 |

FOREIGN PATENT DOCUMENTS

| | | |
|---|---|---|
| JP | 2002-17680 A | 1/2002 |
| JP | 2015-066084 A | 4/2015 |
| WO | 2015-091796 A2 | 6/2015 |
| WO | 2015/180923 A1 | 12/2015 |

OTHER PUBLICATIONS

May 7, 2018 Extended Search Report issued in European Application No. 17205187.2.

(Continued)

*Primary Examiner* — William R Alexander
*Assistant Examiner* — Henry A Duong
(74) *Attorney, Agent, or Firm* — Oliff PLC

(57) ABSTRACT

An ophthalmic apparatus includes: an imaging optical system that includes a light projecting optical system for projecting light to an ACA region of a subject's eye, and a light receiving optical system including a light receiving element for receiving reflected light from the ACA region; an alignment driver configured to change a positional relationship between the subject's eye and the imaging optical system; an imaging processor configured to generate an ACA image based on a signal output from the light receiving element; and a controller configured to detect a feature point in an ACA of the subject's eye from the ACA image, and that adjust the positional relationship in accordance with a position of the feature point in the ACA image.

17 Claims, 8 Drawing Sheets

(56) References Cited

OTHER PUBLICATIONS

Dorairaj, Syril et al.; "Changing Trends of Imaging in Angle Closure Evaluation;" International Scholarly Research getwork (ISRN) Opthalmology, vol. 2012, pp. 1-7, Jan. 1, 2012 (Jan. 1, 2012).

* cited by examiner

OPHTHALMIC APPARATUS

BACKGROUND

The present disclosure relates to an ophthalmic apparatus for obtaining an ACA image of a subject's eye.

In glaucoma diagnosis, it is useful to observe an anterior chamber angle (hereinafter, simply referred to as an ACA) of the subject's eye. In the related art, the ACA is visibly observed by an examiner via a gonioscope. However, in recent years, various apparatuses for imaging the ACA have been proposed.

For example, WO2015/180923 discloses an apparatus which illuminates the ACA of the subject's eye with illumination light so as to obtain a reflected image of the ACA, based on reflected light from the ACA.

SUMMARY

However, in the related art, a method of aligning an optical system of an apparatus with the subject's eye has not been sufficiently reviewed.

In addition, according to the apparatus in the related art, the examiner needs to visibly confirm whether or not a desired observation target is properly projected in a captured image of the ACA. In addition, a focus state of the apparatus needs to be adjusted by the examiner, depending on the desired observation target, consequently, the examiner feels inconvenient.

The present disclosure is made in view of the problems in the related art. In order to solve the problems, the present disclosure aims to provide an ophthalmic apparatus capable of satisfactorily aligning a subject's eye with an optical system by obtaining an ACA image of the subject's eye.

The aspect of the present disclosure provides the following configurations:

An ophthalmic apparatus comprising:
an imaging optical system that includes a light projecting optical system for projecting light to an ACA region of a subject's eye, and a light receiving optical system including a light receiving element for receiving reflected light from the ACA region;
an alignment driver configured to change a positional relationship between the subject's eye and the imaging optical system;
an imaging processor configured to generate an ACA image based on a signal output from the light receiving element; and
a controller configured to detect a feature point in an ACA of the subject's eye from the ACA image, and that adjust the positional relationship in accordance with a position of the feature point in the ACA image.

An ophthalmic apparatus comprising:
an imaging optical system that includes a light projecting optical system for projecting light to an ACA region of a subject's eye, and a light receiving optical system including a light receiving element for receiving reflected light from the ACA region;
a focus changing unit configured to drive a portion of the imaging optical system to change a focus state of the reflected light in the light receiving element;
an imaging processor configured to generate an ACA image, based on a signal output from the light receiving element; and
an image processing unit configured to obtain evaluation information of the focus state based on image information of the ACA image.

An ophthalmic apparatus comprising:
an imaging optical system that includes an objective optical system which bends the light emitted from a light source to tilt an imaging optical axis relative to a fixation optical axis and guide the light to the ACA region of the subject's eye, and a light receiving element configured to emit illumination light to a tissue surface of the ACA region via the objective optical system, and receive reflected light from the tissue surface;
an image acquisition unit configured to acquire an ACA image which is a reflected image based on the reflected light from the tissue surface; and
an image processing unit configured to process the ACA image to detect a feature point in an ACA of the subject's eye from the ACA image.

According to the present disclosure, a subject's eye can be satisfactorily aligned with an optical system by obtaining an ACA image of the subject's eye.

DESCRIPTION OF ILLUSTRATIVE EMBODIMENTS

Outline

Figure 1:
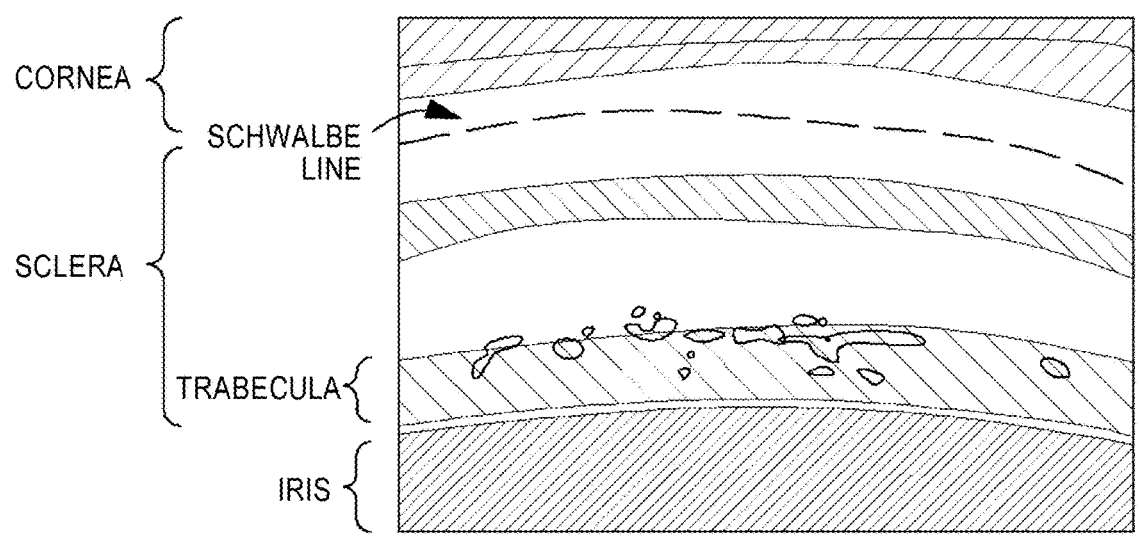
FIG. 1 is a view illustrating an ACA image captured by an ophthalmic apparatus according to an embodiment.

Hereinafter, an ophthalmic apparatus according to the present disclosure will be described with reference to an embodiment.

Detection Process of Feature Point

The ophthalmic apparatus detects a feature point in an ACA (Anterior Chamber Angle) of a subject's eye from an ACA image. The ACA image may be a reflected image (refer to FIG. 1) formed (captured), based on reflected light from an ACA region of the subject's eye. The ACA region may be the ACA of the subject's eye and a region including the vicinity. Specifically, ACA region may be iridocorneal region including at least ACA.

For example, the feature point may be a trabecula. In addition, as the feature point, any one of a Schwalbe line, a scleral spur, a ciliary zone, and an iris may be detected. In addition, in a case where the subject's eye suffers from desquamation syndrome, a pigmentation line (Sampaolesi line) which is likely to appear ahead of the Schwalbe line may be detected as the feature point.

The feature point may be detected by performing image processing on the ACA image. The image processing may be performed by a processor which performs a control operation of the overall apparatus, or may be performed by an image processing processor separate from the processor. In a case where the feature point is detected by performing the image processing, the feature point is detected by using an image feature belonging to the feature point. A detection method conforming to the ACA image and the image feature of the feature point may be appropriately adopted from among detection methods using various pieces of image information such as patterns of contrast, luminance, and shade in the ACA image.

Here, it is conceivable that each subject's eye may have the different luminance or contrast of the feature point in the ACA image depending on a color of the iris. Therefore, for example, the ophthalmic apparatus may detect the feature point by performing a detection process in accordance with the color of the iris. For example, in a case where the feature point is detected using a threshold value, the threshold value may be set in accordance with the color of the iris of the subject's eye. In addition, for example, in a case where the ACA image is a color image having color components of three colors (for example, three colors of RGB), in accordance with the color of the iris of the subject's eye, the balance of RGB in the ACA image may be adjusted, and the feature point may be detected from the adjusted image. Alternatively, any one of RGB components may be selected in accordance with the color of the iris, and the feature point may be detected from an image having the selected component.

In this case, the color of the iris in the subject's eye may be automatically detected from the ACA image in a case where the ACA image is the color image. In this manner, the apparatus may acquire the feature point. In addition, an input interface of the ophthalmic apparatus may be operated so as to input the color of the iris to the apparatus. In addition, the color of the iris may be acquired as data preliminarily registered in electronic medical records of an examinee.

For example, detection results of the feature point in the ACA image may be used in order to adjust imaging conditions in the ophthalmic apparatus. In addition, for example, the detection results of the feature point may be used in order to obtain reference information for an examiner to obtain clinical findings from the ACA image. As a matter of course, the detection results of the feature point in the ACA image may be used for other purposes.

Imaging Optical System

The ophthalmic apparatus may have an imaging optical system in order to capture the ACA image.

The imaging optical system projects light to an ACA region along an imaging optical axis, and receives the light returning from the ACA region.

The imaging optical system may be configured so that the light is emitted to an entire imaging range in a surface texture of the ACA and a light receiving element receives the light returning from the imaging range. In this case, the light receiving element may be a two-dimensional light receiving element. The two-dimensional light receiving element captures the image of the ACA which is formed on a light receiving surface, as the ACA image. However, the imaging optical system is not necessarily limited thereto. For example, the imaging optical system may be an optical system using line scanning or two-dimensional scanning. In this case, scanning (line scanning or two-dimensional scanning) is performed using the light. In this manner, the ACA image is generated by an image processing unit, as the result of receiving the returning light for each scanning.

The imaging optical system has at least a light projecting optical system and a light receiving optical system. The light projecting optical system projects the light to the ACA region of the subject's eye. The light projected from the light projecting optical system may be visible light or invisible light (for example, infrared light). In addition, the projected light may be monochromatic light or multicolor light. The light receiving optical system has at least the light receiving element which receives the reflected light from the ACA region.

The imaging optical system may have an imaging optical axis which is tilted relative to a fixation optical axis and faces the ACA region. The light is projected to and received from the ACA region via the imaging optical axis. For example, the fixation optical axis is a projection optical axis of a fixation target for the subject's eye. In a case where the fixation target is projected, the ophthalmic apparatus may further have a fixation optical system for projecting the fixation target.

The imaging optical system may have the following objective optical system. That is, an objective optical system may be disposed which bends the light emitted from a light source so as to tilt the imaging optical axis relative to the fixation optical axis and to guide the light to the ACA region of the subject's eye. The objective optical system in the imaging optical system may be a reflective system. That is, the objective optical system may include a member which reflects the light such as a mirror or a prism. The objective optical system may be placed closest to the subject's eye in the imaging optical system. The objective optical system causes the light emitted from the light source and travelling outward from the inside of the apparatus to be bent (for example, reflected) toward the fixation optical axis. In this manner, the imaging optical axis tilted relative to the fixation optical axis may be formed. The objective optical system is not necessarily limited to the reflective system. The objective optical system may be partially or entirely formed from a refractive system (for example, a lens system).

Imaging Processor

The imaging processor generates an ACA image, based on a signal output from the light receiving element. For example, as the imaging processor, a processor which controls an operation of the ophthalmic apparatus may be used, or a dedicated image processing IC may be used. The image processing IC may be integrated with the light receiving element.

The imaging processor generates at least the ACA image as a still image. The ACA image generated by the imaging processor may be displayed on a monitor or may be stored in a nonvolatile memory. In addition, the imaging processor may generate the ACA image captured in time series, based on signals sequentially output from the light receiving element. In this case, the ACA image captured in time series may be displayed on the monitor, for example, as a live image (real-time moving image). In addition to the observation of the ACA region observed by the examiner, the ACA image captured in time series may be used for at least any one of focus adjustment and alignment adjustment (to be described later).

Switching Imaging Position of ACA Image

The ophthalmic apparatus may further have a switching unit which displaces an imaging position in the imaging optical system for an entire periphery of the ACA. The switching unit is disposed, thereby enabling the ACA image to be captured at a plurality of imaging positions in the entire periphery of the ACA.

The switching unit may displace an orientation of the imaging optical axis with respect to the fixation optical axis so that the ACA image is captured by the imaging optical system at two or more imaging positions having mutually different radial directions. As a specific example, in a case where the imaging optical axis is tilted relative to the fixation optical axis, for example, the switching unit may rotate the imaging optical axis around the fixation optical axis. The switching unit may rotate the imaging optical axis around the fixation optical axis by partially or entirely rotating the imaging optical system around the fixation optical axis. In this case, the switching unit may have a drive source. The drive source includes a motor as an example.

The switching unit is not necessarily limited thereto. For example, instead of rotating the imaging optical axis tilted relative to the fixation optical axis around the fixation optical axis, the switching unit may adopt a configuration in which fixation is induced so that the orientation of the line of sight of the subject's eye is greatly displaced, a configuration in which a three-dimensional positional relationship is adjusted between the subject's eye and the apparatus. Alternatively, a configuration may be adopted in which both of these are combined with each other.

Focus Changing Unit

The ophthalmic apparatus may further have a focus changing unit. The focus changing unit drives a portion of the imaging optical system so as to change a focus state of the reflected light in the light receiving element. The focus changing unit displaces an optical member (that is, a portion of the imaging optical system) placed in an optical path of the imaging optical system. In this manner, a position of a conjugate plane of the ACA region is displaced along the optical path. For example, the optical member displaced in the focus changing unit may be a focus lens, or may be a variable focus lens (for example, a liquid crystal lens or a liquid lens). Alternatively, any other optical member may be used. The focus state may be manually adjusted, or may be automatically adjusted by a controller.

Operation Relating to Focus

The ophthalmic apparatus may have the image processing unit. For example, the image processing unit obtains evaluation information of the focus state, based on image information of the ACA image. The image information of the ACA image may partially or entirely include the image information of the ACA image. In the ACA image, a region processed to obtain the evaluation information of the focus state can be appropriately set within an allowable range of the depth of field of the imaging optical system. For example, even if there is a height difference on a surface of the ACA, as the depth of field increases, the region to be processed can be more widely set.

Here, the image information may include luminance information for each pixel. For example, the evaluation information of the focus state acquired by the image processing unit may be contrast, histogram, differential histogram, or image edge strength. For example, as the contrast becomes higher in a certain region, the region is brought into a highly in-focus state. Various image processing methods are known as methods of obtaining the above-described evaluation information from the image information in a prescribed area, and any one of the image processing methods may be adopted.

Hereinafter, as an example of the method of obtaining the evaluation information of the focus state, based on a portion of the ACA image, a method of obtaining the evaluation information of the focus state, based on the image information relating to the feature point of the ACA image will be described. The image information relating to the feature point may include the image information in a neighboring region of the feature point.

The feature point (for example, any one of the trabecula, the Schwalbe line, the scleral spur, the ciliary zone, the iris, and the pigmentation line) of the ACA which is included in the ACA image can be used as a useful observation target in order to obtain clinical findings relating to the ACA. Therefore, hereinafter, a method of acquiring the ACA image focused on the feature point by using the evaluation information will be described as an example.

Drive Control of Focus Changing Unit, Based on Evaluation Information

The ophthalmic apparatus may further have the controller which drives the focus changing unit, based on the evaluation information of the focus state acquired by the image processing unit. In this case, the controller may drive the focus changing unit so as to be focused on the feature point. An example of drive control will be described below. The controller drives the focus changing unit so as to change the focus state, and determines whether the focus state is changed in a direction close to focusing on the feature point or in a direction away from the focusing on the feature point, based on a difference in the evaluation information in the plurality of ACA images captured while the focus state is changed. In a case where the focus state is changed in the direction away from the focusing on the feature point, the controller switches the drive control of the focus changing unit so that the focus state is changed in the direction close to the focusing on the feature point. Then, when the focus changing unit is driven in the direction close to the focusing on the feature point and the focus state is changed in the direction away from the focusing on the feature point (inflection point of the difference in the evaluation information), the controller stops the drive control of the focus changing unit. In this manner, the imaging optical system is focused on the feature point. However, the drive control of the focus changing unit in order to obtain the focusing on the feature point is not necessarily limited thereto.

A still image of the ACA image may be captured again in a state where the focusing on the feature point is obtained. The ACA image obtained at that time may be stored in a nonvolatile memory as an image (captured image) used for obtaining clinical findings. The ophthalmic apparatus may capture the ACA image focused on the feature point by performing this focus adjustment.

In this way, in a case where the ophthalmic apparatus has the switching unit and the imaging position in the imaging optical system for the entire periphery of the ACA can be displaced by the switching unit, the controller of the ophthalmic apparatus may cause the switching unit to switch the imaging position, and may further control the focus state at a plurality of mutually different imaging positions.

Extraction of Image Focused on Feature Point from ACA Image

The ACA image focused on the feature point may be acquired by means different from the drive control of the focus changing unit based on the evaluation information.

For example, a method may be used in which the ACA image focused on the feature point is selected (extracted) from the plurality of previously captured ACA images, that is, the ACA images having the mutually different focus states. The image processing unit obtains the evaluation information of the focus state from each of the plurality of ACA images having the mutually different focus states. Then, the selection unit in the ophthalmic apparatus selects the ACA image focused on the feature point from among the plurality of the ACA images, based on the evaluation information of each ACA image. In this case, for example, the selection unit may be shared with either the image processing unit or the processor which controls the operation of the ophthalmic apparatus.

The plurality of ACA images having the mutually different focus states may be acquired at each imaging position. In this case, the imaging unit is switched by the switching unit, and the ACA image is acquired at each imaging position as a result of controlling the focus state at the plurality of mutually different imaging positions.

Manual Adjustment of Focus State

In addition, the focus state in the imaging optical system may be manually adjusted by the examiner, based on the evaluation information of the focus state obtained from the ACA image.

In this case, for example, together with the live image of the ACA image, the evaluation information of the focus state for the feature point of the ACA image is displayed on the monitor. In addition, the adjustment amount of the focus state in the focus changing unit can be set to be any desired adjustment amount based on the operation on an input interface. In this case, the evaluation information may be displayed in association with the feature point on the monitor. Referring to the evaluation information on the monitor, the examiner operates the focus changing unit. In this manner, the examiner can properly perform the adjustment in a state where the focus changing unit is focused on the feature point.

Alignment Driver

The ophthalmic apparatus may further have an alignment driver. The alignment driver changes a positional relationship between the subject's eye and the imaging optical system. In this case, alignment adjustment is performed by relatively moving the subject's eye and the imaging optical system. The alignment driver may change the positional relationship in any direction of a forward/rearward direction, a rightward/leftward direction, and an upward/downward direction.

For example, the alignment driver may move the imaging optical system relative to the subject's eye. The alignment driver may be a mechanical mechanism, a mechanism that moves the imaging optical system by using an electric actuator, or a mechanism including both of these. The alignment driver may be manually driven in response to the operation of the operation unit (for example, a joystick), or may be automatically driven, based on the ACA image, for example.

Operation Relating to Alignment

The ophthalmic apparatus may further have a controller (alignment controller) which detects the feature point in the ACA of the subject's eye from the ACA image and adjusts the positional relationship between the subject's eye and the imaging optical system in accordance with the position of the feature point in the ACA image. That is, the controller may adjust the imaging position with reference to the feature point in the ACA.

The controller may perform the drive control on the alignment driver so as to cause the alignment driver to change the positional relationship between the subject's eye and the imaging optical system. In addition, the controller may manually change the positional relationship between the subject's eye and the imaging optical system by outputting information for guiding the operation of the operation unit to the monitor.

First, a method will be described in which the apparatus automatically performs the alignment by performing the drive control of the alignment driver. In this case, for example, the controller may obtain a deviation amount (displacement amount) between a predetermined target position in the ACA image and the position of the feature point detected from the ACA image. In this manner, based on the deviation amount, the alignment driver may be driven.

Here, as an example, an operation method in a case where the imaging optical system has the following imaging optical axis and the reflected image of the ACA is generated by the imaging processor will be described. The imaging optical axis in this case is tilted relative to the fixation optical axis, and faces the ACA region.

The controller performs the drive control on the alignment driver in accordance with the position of the feature point in the ACA image, that is, the position in the radial direction around a fixation optical axis L1. In this manner, the controller adjusts the positional relationship between the subject's eye and the imaging optical system. For example, the alignment driver is driven, based on the deviation amount between the feature point and the target position in the radial direction. More specifically, the alignment driver is driven by the controller as much as a drive amount which eliminates the deviation amount between the feature point and the target position in the radial direction. Here, in each case of a case where the positional relationship between the subject's eye and the imaging optical system is changed in the anterior-posterior direction and in the forward/rearward direction and a case where the positional relationship is changed in the radial direction, the position in the radial direction of the feature point in the ACA image is changed. Therefore, the controller adjusts one or both of the positional relationships between the subject's eye and the imaging optical system in the forward/rearward direction and in the radial direction.

Furthermore, in a case where the switching unit of the imaging position is driven so that two ACA images can be captured at two imaging positions symmetrical with respect to the fixation optical axis, the controller may control the positional relationship between the subject's eye and the imaging optical system so that the feature points in the ACA images are placed at the same position in the radial direction (in other words, a position symmetrical with respect to the fixation optical axis). In this case, the controller adjusts at least the positional relationship between the subject's eye and the imaging optical system in the radial direction in the two ACA images. In this manner, the feature point in the two ACA images can be placed at the same position in the radial direction.

Two ACA images (third and fourth ACA images) may be further captured at the imaging position different from the imaging position where the two ACA images (first and second ACA images), that is, the two imaging positions symmetrical with respect to the fixation optical axis. In this manner, the positional relationship between the subject's eye and the imaging optical system may be similarly adjusted. As a result of this alignment adjustment, for example, in a case where the imaging position is changed by driving the switching unit, the feature point is satisfactorily imaged at each imaging position.

Furthermore, the positional relationship between the subject's eye and the imaging optical system may be adjusted in an operating distance direction (forward/rearward direction, along the fixation optical axis). For example, the positional relationship in the operating distance direction may be adjusted so that any one of both the position of the feature point in the first and second ACA images in the radial direction and the position of the feature point in the third and fourth ACA images in the radial direction is placed at the above-described target position. In addition, for example, the positional relationship in the operating distance direction may be adjusted so that an intermediate position (for example, an average position) between both positions is placed at the above-described target position.

Manual Alignment Adjustment

In addition, the alignment of the imaging optical system with the subject's eye may be manually adjusted by the examiner, based on the position of the feature point in the ACA image. In this case, the operation unit is operated by the examiner, thereby causing the positional relationship between the subject's eye and the imaging optical system to be adjusted in accordance with the operation. In addition, the controller (alignment controller) outputs information (hereinafter, referred to as guidance information) for guiding the operation of the operation unit, based on the position of the feature point in the ACA image. For example, the guidance information may be information for guiding a direction to move the imaging optical system. For example, the guidance information may be displayed on the monitor as an arrow graphic or a text indicating "up" and "down". As a matter of course, the guidance information is not limited to visual information output to the monitor, and may be voice or output information from another output device disposed in the ophthalmic apparatus.

Combination of Automatic Alignment Adjustment and Manual Alignment Adjustment

When the alignment adjustment is performed in the upward/downward and rightward/leftward directions and the operating distance direction, the alignment may be automatically adjusted in the upward/downward and rightward/leftward directions by the controller. The alignment may be manually adjusted in the operating distance direction, based on the operation of the examiner. This reduces possibilities that the apparatus may be located too close to the subject's eye against the will of the examiner. In this case, a controller 80 may adjust the alignment in the upward/downward and rightward/leftward directions by driving the alignment driver, based on the position of the feature point, and may output the guide information for guiding the operation relating to the manual alignment in the operating distance direction.

In this case, the alignment driver has a mechanical drive mechanism and an electric drive mechanism. The mechanical drive mechanism may adjust the positional relationship between the subject's eye and the imaging optical system in the operating distance direction, and the electric drive mechanism may adjust the positional relationship in the upward/downward and rightward/leftward directions.

Embodiment

Hereinafter, an embodiment of the ophthalmic apparatus according to the present disclosure will be described with reference to the drawings. An ophthalmic apparatus 1 according to the embodiment is a gonioscopic imaging apparatus. The ophthalmic apparatus 1 captures a reflected image (refer to FIG. 1) of the ACA of the subject's eye.

Apparatus Configuration

Figure 2:
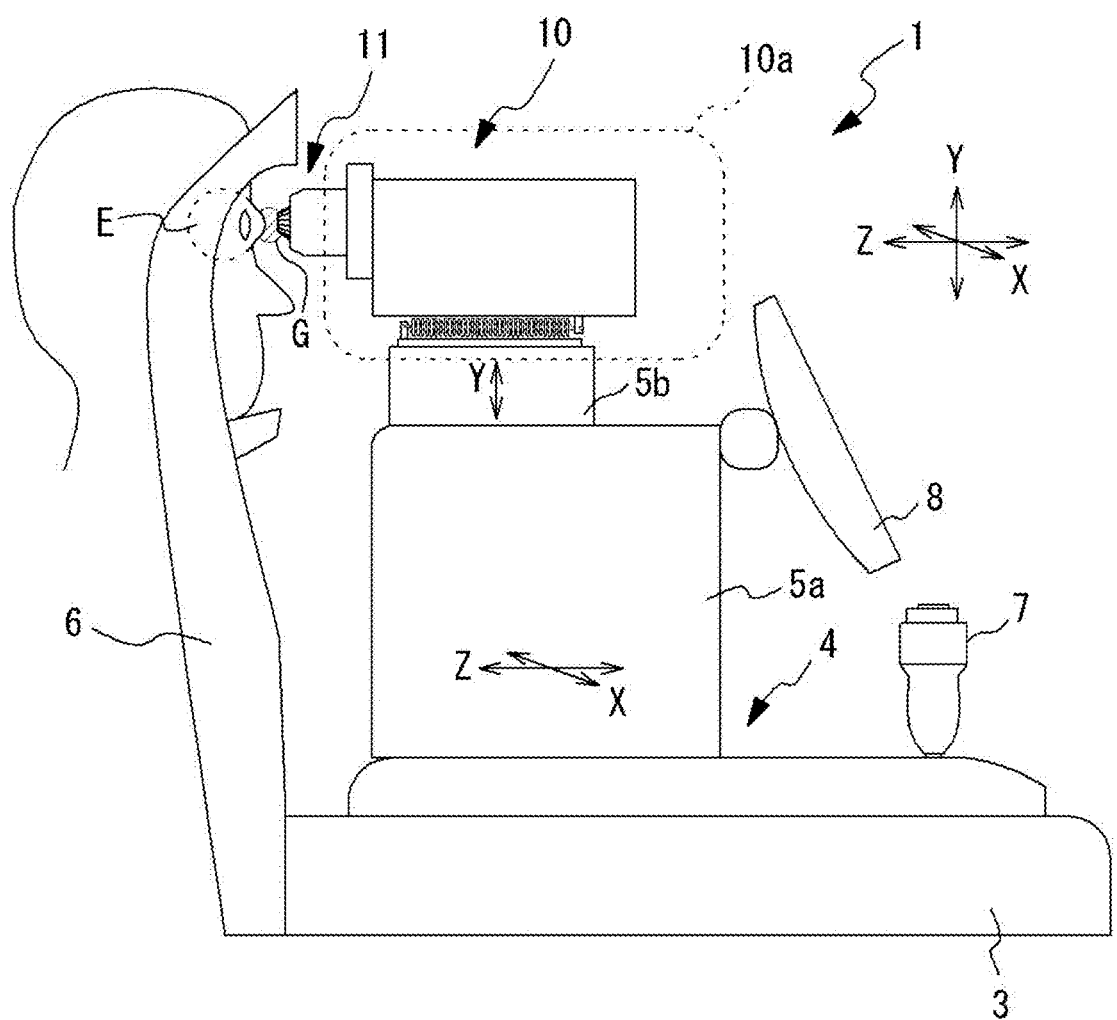
FIG. 2 is a schematic view illustrating a schematic configuration of the ophthalmic apparatus according to the embodiment.

Referring to FIG. 2, a schematic apparatus configuration in the ophthalmic apparatus 1 will be described. In the following description, it is assumed that an X-direction illustrated in FIG. 2 is the rightward/leftward direction, a Y-direction is the upward/downward direction, and a Z-direction is the forward/rearward direction.

The ophthalmic apparatus 1 emits illumination light in an oblique direction with respect to a visual axis of a subject's eye E. Then, the ophthalmic apparatus 1 receives the reflected light from the ACA region along the imaging optical axis. In this manner, the ophthalmic apparatus 1 captures the reflected image in the ACA region of the subject's eye, as an ACA image.

As illustrated in FIG. 1, the ophthalmic apparatus 1 has a base 3, alignment mechanisms 4, 5a, and 5b, a face support unit 6, a joystick 7, a monitor 8, and an optical unit 10.

The optical unit 10 has a main optical system used for capturing the reflected image of the ACA. Details of the optical system will be described later with reference to FIG. 3. In the embodiment, the optical unit 10 is accommodated inside a cover 10a. However, a distal end portion 11 is exposed outward from the cover 10a.

The base 3 supports the alignment mechanisms 4, 5a, and 5b and the face support unit 6.

The alignment mechanisms 4, 5a, and 5b in the present embodiment are roughly divided into a movable base 4 and XYZ-drivers 5a and 5b. Among them, the movable base 4 is operated by a mechanical mechanism, and the XYZ-drivers 5a and 5b are operated by an electric actuator.

The movable base 4 is disposed on the base 3, and has a mechanical moving mechanism between the base 4 and the movable base 4. This moving mechanism moves the movable base 4 in the XZ-direction. As a result, the positional relationship between the subject's eye E and the optical unit 10 is adjusted in the XZ-direction. The examiner moves the movable base 4 with respect to the base 3 by operating the joystick 7.

The XYZ-drivers 5a and 5b in the present embodiment are stacked on the movable base 4. Based on a control signal from the controller 80 (refer to FIG. 4) of the ophthalmic apparatus 1, the XYZ-drivers 5a and 5b move the optical unit 10 in each XYZ-direction. As a result, the positional relationship between the subject's eye E and the optical unit 10 is adjusted in each XYZ-direction.

The monitor 8 is placed on a housing side surface on the examiner side. The monitor 8 may be a display unit for displaying the ACA image captured via the optical unit 10.

Optical System

Figure 3:
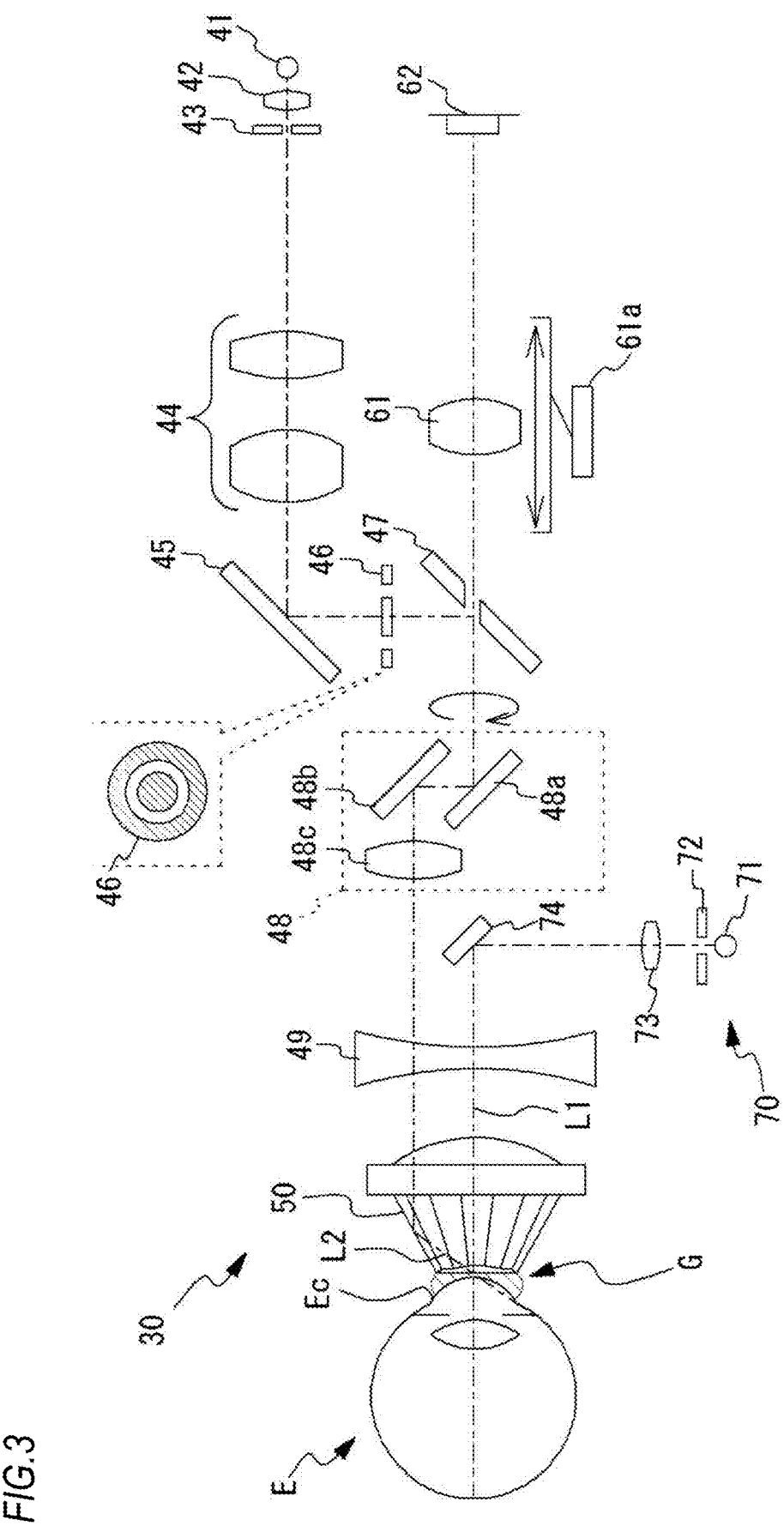
FIG. 3 is a perspective view illustrating an example of an imaging optical system.

Next, referring to FIG. 3, the optical system disposed in the optical unit 10 will be described. The optical unit 10 has at least an imaging optical system 30. Furthermore, in the present embodiment, the optical unit 10 has a fixation optical system 70.

For convenience of description, the fixation optical system 70 will be first described. The fixation optical system 70 has at least a fixation light source (fixation target) 71. In addition, in FIG. 3, the fixation optical system 70 further has an aperture 72, a lens 73, and a mirror 74. The light emitted from the light source 71 is collimated with a predetermined luminous flux diameter by passing through the lens 73 via the aperture 72. The collimated light is bent by the mirror 74, and is projected to the subject's eye E. In FIG. 3, an optical axis of the fixation optical system 70 (more specifically, a range from the mirror 74 to the subject's eye E in the optical axis of the fixation optical system 70) is represented by a reference numeral L1. The reference numeral L1 is referred to as a fixation optical axis. Each member of the imaging optical system 30 illustrated in FIG. 3 is disposed with reference to the fixation optical axis.

The imaging optical system 30 has a light projecting optical system 40 and a light receiving optical system 60. In addition, the imaging optical system 30 has an imaging optical axis L2. The imaging optical axis L2 is tilted relative to the fixation optical axis L1, and faces the ACA of the subject's eye E.

The light projecting optical system 40 has at least an object reflection unit 50 and an optical deflection unit 48. In addition, in the embodiment, the light projecting optical system 40 has a light source 41, a lens 42, an aperture 43, a lens 44, a mirror 45, a ring aperture 46, a perforated mirror 47, and a lens 49.

The light source 41 serves as a light source of illumination light emitted to the ACA. In the present embodiment, the light source 41 emits visible light. In the following description, in order to obtain the ACA image as a color image, it is assumed that at least light with a plurality of colors (for example, white light) having different wavelength ranges can be emitted.

The light (illumination light) emitted from the light source 41 is transmitted via the lens 42, the aperture 43, the lens 44, the mirror 45, the ring aperture 46, and the perforated mirror 47, and is incident on the optical deflection unit 48.

Here, the ring aperture 46 is disposed in order to suppress stray light caused by reflection inside the imaging optical system 30. For example, the reflection on the surface on the light source 41 side of the lens 48c and the lens 49 is suppressed by the ring aperture 46.

In addition, the perforated mirror 47 is an example of an optical path dividing portion which divides the optical path into the light projecting optical system 40 and the light receiving optical system 60. Instead of the perforated mirror 47, other beam splitters such as a half mirror may be employed. In the present embodiment, the light emitted from the light source 41 is reflected on a mirror surface of the perforated mirror 47 so as to be oriented toward the optical deflection unit 48.

In the present embodiment, the optical path center of the illumination light reflected on the perforated mirror 47 is coaxial with the fixation optical axis L1.

The optical deflection unit 48 deflects the optical path of the illumination light with respect to the fixation optical axis L1. In the present embodiment, the optical path center of the illumination light is shifted as far as a predetermined distance with respect to the fixation optical axis L1 by using the two mirrors 48a and 48b disposed in parallel. The shifted illumination light passes through the lens 48c, and is emitted outward from the optical deflection unit 48.

The lens 49 and the object reflection unit 50 are disposed at a position where the respective optical axes are away from the optical path center of the illumination light deflected by the optical deflection unit 48. In the present embodiment, the respective optical axes in the lens 49 and the object reflection unit 50 are disposed coaxially with the fixation optical axis L1.

The lens 49 has negative power. The lens 49 causes the illumination light emitted substantially parallel to the fixation optical axis L1 from the optical deflection unit 49 to be bent in a direction away from the fixation optical axis L1, and causes the illumination light to be incident on the object reflection unit 50.

The object reflection unit 50 has a reflection surface which bends the illumination light toward the fixation optical axis L1 side. The optical axis of the illumination light reflected on the reflection surface is bent so as to be greatly tilted relative to the fixation optical axis L1, and is guided outward from the apparatus. In this case, the optical axis guided outward from the apparatus is used as the imaging optical axis L2 in the present embodiment. The illumination light from the apparatus is emitted to the ACA region of the subject's eye E along the imaging optical axis L2.

In the present embodiment, a plurality of reflection surfaces are disposed side by side around the optical axis in the object reflection unit 50. As a specific example of the object reflection unit 50, the present embodiment employs a frustum-shaped prism whose bottom surface has a regular polygon, for example. More specifically, the present embodiment employs a prism whose bottom surface is a regular hexadecagon and which has 16 side surfaces. In the present embodiment, the reflection surfaces facing the fixation optical axis L1 are disposed in the directions of 0°, 22.5°, 45°, 67.5°, 90°, (omitted) . . . , and 337.5° when viewed from the subject's eye E. Each angle is set with reference to the fixation optical axis L1. In addition, for convenience of description, 0° is set on a horizontal plane.

However, the reflection surface does not necessarily need to be divided into a plurality of pieces, and may be formed using a series of curved surfaces. In addition, the object reflection unit 50 does not necessarily need to be a prism, and may be a reflection mirror, for example. In a case of the reflection mirror, a cylindrical polygonal mirror or a curved mirror having the reflection surface on the optical axis side may be used.

Here, the ophthalmic apparatus 1 according to the present embodiment has a driver 48d (refer to FIG. 4) for rotating the optical deflection unit 48 around the fixation optical axis L1. In response to the rotation of the optical deflection unit 48, an incident position of the illumination light on the lens 49 and the object reflection unit 50 is rotated around the fixation optical axis L1. As a result, the imaging optical axis L2 is rotated around the fixation optical axis L1. Consequently, the emitting position of the illumination light in the entire periphery of the ACA is displaced.

In the present embodiment, a gel G is interposed between the object reflection unit 50 (prism) and the cornea. The gel G is applied to the cornea in order to suppress the corneal reflection of the illumination light. The gel G may be in contact with both the cornea and the distal end of the object reflection unit 50 in a state where a holding container (not illustrated) is filled with the gel G (for more details, refer to JP-A-2002-17680).

The illumination light emitted by the light projecting optical system 40 is reflected on the ACA region, and is guided along the imaging optical axis L2 to the light receiving optical system 60 inside the apparatus.

In the present embodiment, the light receiving optical system 60 has at least an image sensor (an example of the light receiving element) 62. In addition, the light receiving optical system 60 shares the object reflection unit 50 and the perforated mirror (beam splitter) 47 at least with the light projecting optical system 40. Furthermore, the optical deflection unit 48 and the lens 49 may be shared with the light projecting optical system 40. In addition, the light receiving optical system 60 has a focus lens 61. The focus lens 61 is a portion of the focus changing unit in the imaging optical system 30 according to the present embodiment. A driver 61*a* for moving the focus lens 61 along the optical axis is disposed in the ophthalmic apparatus 1. The driver 61*a* may include a linear actuator, for example.

The reflected light from the ACA region is emitted to the perforated mirror 47 via the object reflection unit 50, the lens 49, and the optical deflection unit 48. Thereafter, the reflected light passes through each of the opening of the perforated mirror 47 and the focus lens 61, and forms an image in the image sensor 62. As a result, the ACA image in which the illumination light emitted portion serves as the imaging position in the entire periphery of the ACA is obtained, based on the light receiving signal from the image sensor 62.

In addition, the optical deflection unit 48 is rotated, and the imaging optical axis L2 is rotated around the fixation optical axis L1. In this manner, it is possible to switch the imaging position in the entire periphery of the ACA. As described above, in the present embodiment, the object reflection unit 50 has the sixteen reflection surfaces. Accordingly, the entire periphery of the ACA can be divided into sixteen pieces, and each piece can be selectively imaged.

Control System

Figure 4:
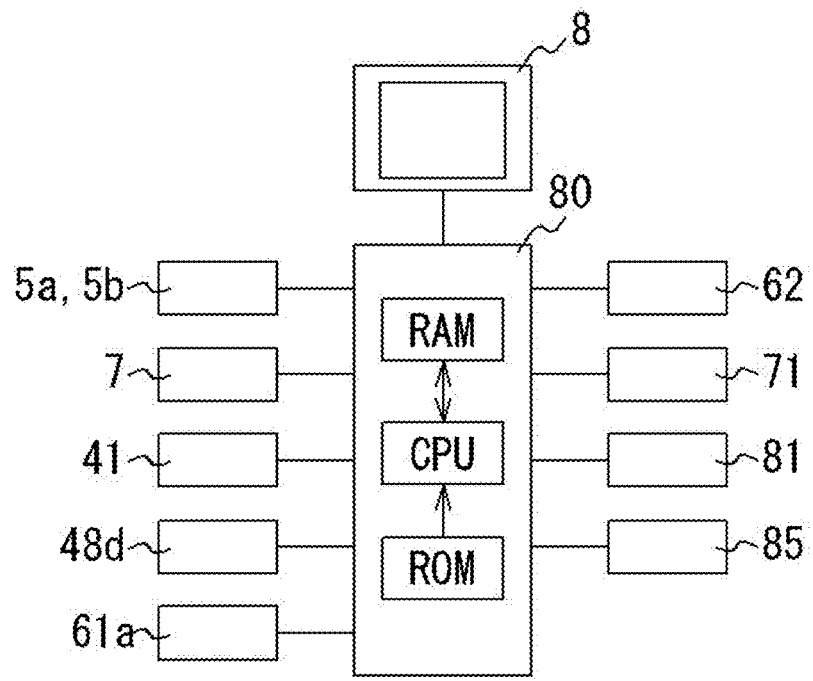
FIG. 4 is a block diagram illustrating an example of a control system.

Next, referring to FIG. 4, a control system of the ophthalmic apparatus 1 will be described. The ophthalmic apparatus 1 includes a controller (processor) 80. The controller 80 performs an overall control process and various arithmetic processes of the apparatus.

The controller 80 may include a CPU, a ROM, and a RAM. For example, the RAM stores temporary data used for imaging and measurement.

For example, the controller 80 is connected to the alignment mechanisms 5*a* and 5*b*, the monitor 8, the light source 41, the driver 48*d*, the driver 61*a*, the light receiving element 62, the light source 71, the storage device 81, and the operation unit 85.

The storage device 81 is a rewritable nonvolatile storage device. As the storage device 81, various storage devices such as a hard disk, a flash memory, and USB memory can be employed. In addition, for example, the storage device 81 may store at least a program for causing the ophthalmic apparatus 1 to execute various operations such as the imaging operation.

The ACA image captured by the ophthalmic apparatus 1 may be stored in the storage device 81, or may be displayed on the monitor 8.

The operation unit 85 is an input interface in the ophthalmic apparatus 1. The operation unit 85 is operated by the examiner. In this manner, an instruction corresponding to the operation is input to the controller 80. As the operation unit 85, for example, a mouse or a pointing device such as a touch panel may be used, or a keyboard may be used. In addition, in the ophthalmic apparatus 1, the joystick 7 operated for alignment may be used as one of the operation units 85.

Description of Operation

Figure 5:
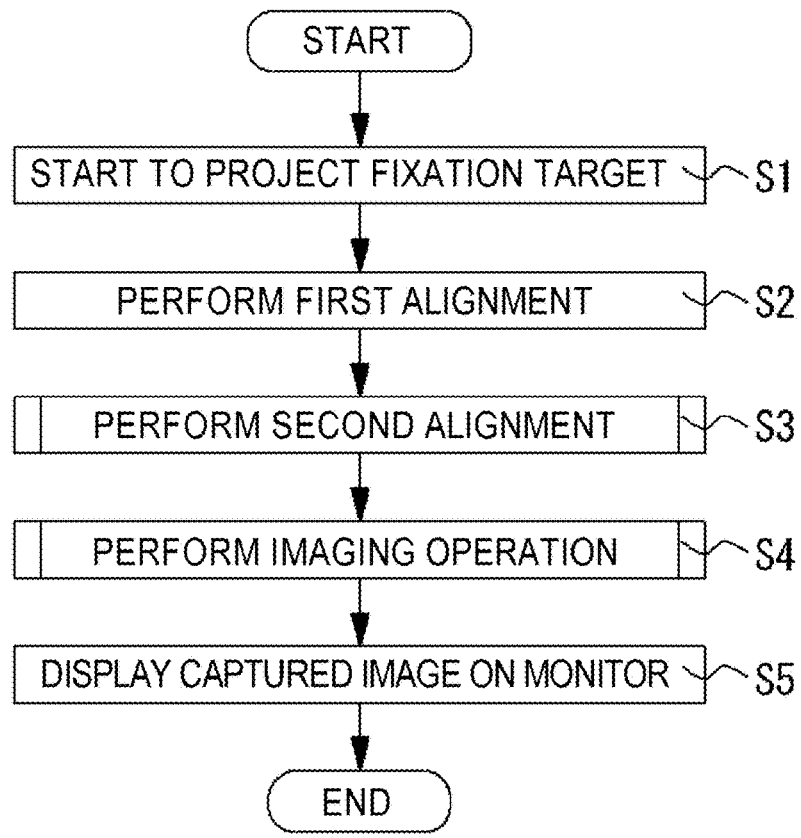
FIG. 5 is a flowchart illustrating an operation of the apparatus.

An imaging operation of the ACA image in the ophthalmic apparatus 1 having the above-described configuration will be described with reference to a flowchart in FIG. 5.

When the imaging operation is performed, the controller 80 first switches on the light source 71, and starts to project a fixation target (S1). In this manner, the line of sight of the subject's eye E is induced.

Then, the examiner operates the joystick 7, and moves the imaging optical system 30 close to the subject's eye E so that the distal end of the object reflection unit 50 is located in a distance of approximately several millimeters from the cornea of the subject's eye E (first alignment (S2)). In this case, the gel G is interposed between the subject's eye E and the object reflection unit 50.

After the first alignment is completed, second alignment is performed (S3). For example, the apparatus may automatically detect the completion of the first alignment, and thereafter, the second alignment may start. Alternatively, a predetermined operation input to the operation unit 85 may be regarded as a trigger, and thereafter, the second alignment may start.

Here, an example of a case where the completion of the first alignment is automatically detected will be described. For example, the controller 80 repeatedly captures the ACA images at a plurality of predetermined imaging positions while the joystick 7 is operated by the examiner. Each of the ACA images is then processed so as to detect whether or not the feature point of the ACA is included in the ACA image. More specifically, the controller 80 confirms whether or not each of the ACA images includes an image feature indicating the feature point of the ACA. The first alignment may be completed in a case where the feature point of the ACA is detected in the ACA image at each imaging position. The feature point used when determining the completion of the first alignment may be the same as the feature point used for the second alignment (to be described later).

In the second alignment, the positional relationship between the subject's eye E and the imaging optical system 30 is adjusted so that the optical axis of the object reflection unit 50 substantially coincides with the center of the entire periphery of the ACA. More specifically, when the ACA images are obtained at the mutually different imaging positions by the rotation of the optical deflection unit 48, the positional relationship is adjusted so that a predetermined feature point is satisfactorily included in each of the ACA images.

Figure 6:
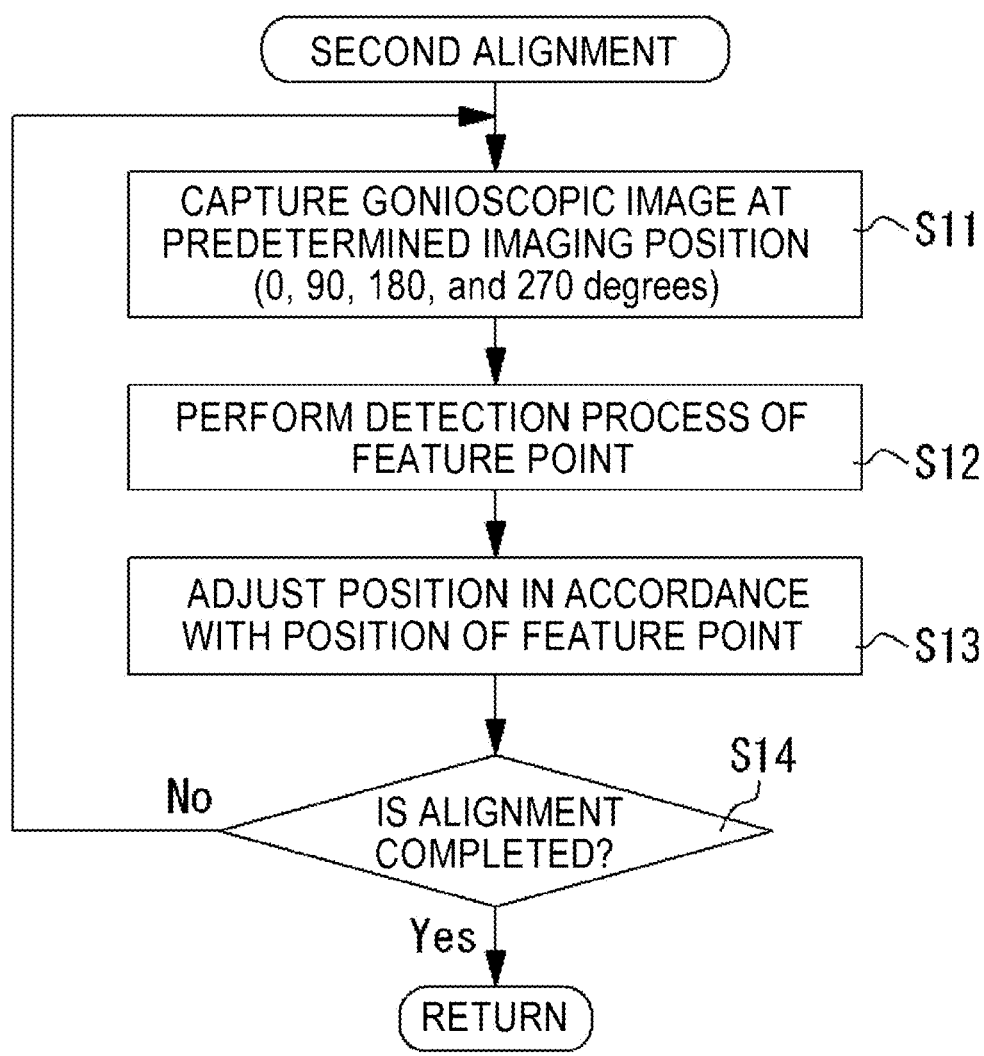
FIG. 6 is a flowchart illustrating an alignment operation.

Here, details of the second alignment will be described with reference to FIGS. 6 to 8.

First, the optical deflection unit 48 is rotated so as to capture the ACA image at a predetermined imaging position (S11). The controller 80 rotates the optical deflection unit 48 from a position of 0° as much as every ¼ round (that is, by 90°). That is, the rotation is temporarily stopped at every rotation of ¼ round.

In addition, the illumination light is emitted from the light projecting optical system 40 at every rotation of ¼ round so as to capture the ACA image. The ACA image may be captured while the rotation is stopped.

As a result, every time the optical deflection unit 48 is rotated as much as one round, the ACA images captured at the positions of 0°, 90°, 180°, and 270° in the entire periphery of the ACA are captured at least one by one. During the alignment, the controller 80 repeatedly rotates the optical deflection unit 48, and repeatedly captures the ACA image.

Figure 7:
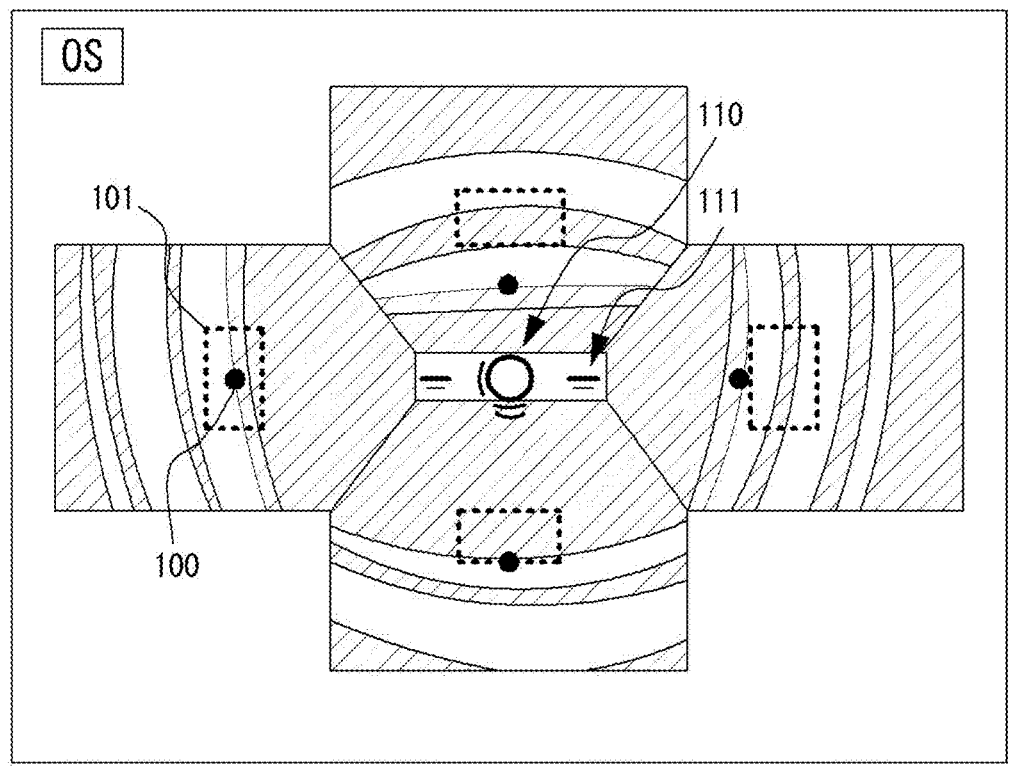
FIG. 7 is a view illustrating a display mode of a screen during alignment.

In this case, as illustrated in FIG. 7, the ACA image captured at each position may be controlled to be simultaneously displayed on the monitor 8. In this case, each of the ACA images may be switched and displayed in time series. In this manner, the examiner can recognize an alignment state.

In FIG. 7, the positional relationship between the respective ACA images displayed on the monitor 8 corresponds to the positional relationship of the imaging portion between the respective ACA images. That is, in the present embodiment, each of the four ACA images captured at the positions of 0°, 90°, 180°, and 270° is displayed at the positions of 0°, 90°, 180°, and 270° with reference to one point on the monitor.

In addition, in the present embodiment, deviation from the alignment target position in each of the X, Y, and Z directions is detected by the controller 80. Then, indicators (illustrated by reference numerals 100, 101, 110, and 111) indicating the detected deviation (that is, the alignment state) are displayed (simultaneously) together with the ACA image of each portion. The indicators are displayed, thereby enabling the examiner to more easily recognize the alignment state. Details of the indicators will be described later. In addition, in the present embodiment, the alignment state indicated by the indicators is recognized in each of the X, Y, and Z directions. However, the configuration is not necessarily limited thereto. The alignment state may be only partially indicated by the above-described indicators.

The controller 80 detects the feature point from the ACA image frequently captured for each imaging portion (S12). Then, in accordance with the position of the detected feature point, the alignment mechanisms 5a and 5b are driven and controlled (S13). Hereinafter, in the present embodiment, it is assumed that the trabecula is detected as the feature point.

Here, referring to FIG. 8, an example of a method of detecting the trabecula from the ACA image will be described. The controller 80 detects the trabecula by using luminance information in the ACA image.

Figure 8:
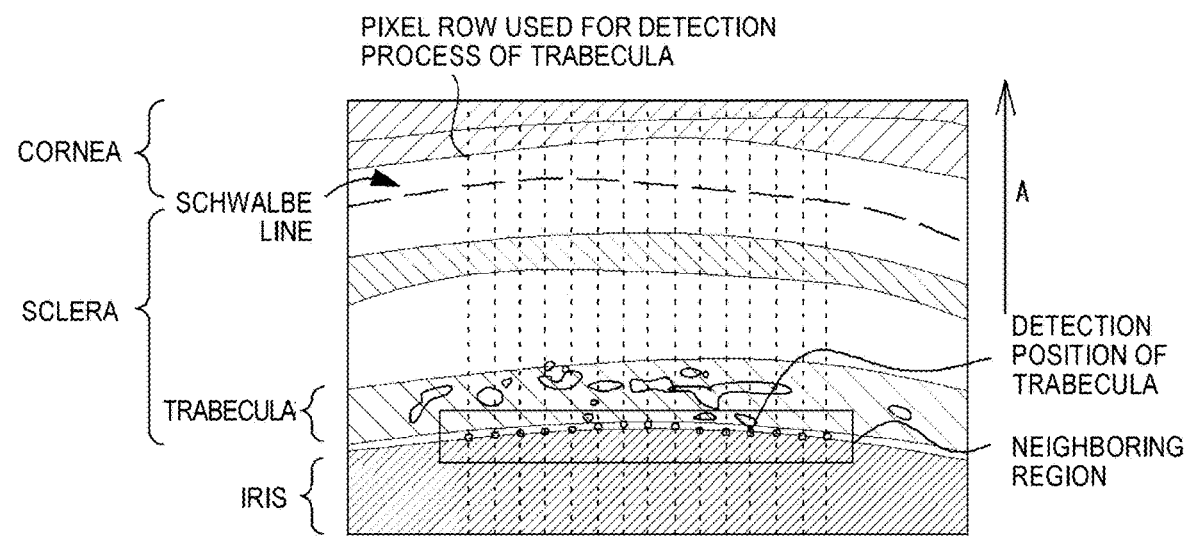
FIG. 8 is a view for describing a detection method of a trabecula and a detection method of a focus state.

In the ACA image illustrated in FIG. 8, a direction of an arrow A indicates the radial direction around the fixation optical axis L1. The luminance of ACA image is changed in accordance with a difference in the imaged portions along the direction of the arrow A.

The trabecula is located between the iris and the cornea. The cornea is more likely to reflect visible light compared to the iris. Accordingly, in each pixel row along the direction of the arrow A in the ACA image, a significantly changed luminance is confirmed in the vicinity of the trabecula.

Therefore, one or more pixel rows along the direction of the arrow A are extracted from the ACA image. The position of the trabecula in the direction of the arrow A is detected based on the luminance information in the extracted pixel row. It is preferable to extract a plurality of pixel rows from one ACA image. In this case, it is preferable that each of the extracted pixel rows is located at a position away from the other extracted pixel row (that is, located away in the rotation direction (direction intersecting the arrow A) around the fixation optical axis L2).

In this case, differential (difference) information on the luminance in the direction of the arrow A may be obtained in the extracted pixel row, and a position where a predetermined luminance change is detected based on the differential (difference) information may be detected as the position of the trabecula.

The differential (difference) information on a certain pixel is obtained by calculating a luminance difference (contrast) between the certain pixel and the pixel whose position in the direction of the arrow A is different as much as a prescribed amount from the certain pixel. For example, the luminance difference between the adjacent pixels may be calculated. The luminance difference is calculated for other pixels within the pixel row, thereby obtaining the differential (difference) information on the luminance in one pixel row.

For example, when the differential (difference) information in the pixel row is viewed along the direction of the arrow A (from the fixation optical axis L1 side to the distal side), a position having the differential (difference) information whose value is equal to or greater than a predetermined threshold value may be detected as the position of the trabecula. In addition, for example, the inflection point of the luminance information may be obtained by further differentiating the differential information, and the inflection point which first appears when viewed along the direction of the arrow A may be detected as the position of the trabecula.

The luminance change at the position of the trabecula varies depending on a color of the iris of the examinee. Therefore, for example, in a case where the position of the trabecula is detected based on the threshold value, the threshold value may be changeable depending on the color of the iris of the examinee.

The position of the trabecula is detected in the plurality of extracted pixel rows. In this manner, the position of the trabecula can be properly detected in the ACA image. In a case where the position of the trabecula detected in a certain pixel row is greatly different from the detection position of the trabecula in the other pixel row, there is a possibility of erroneous detection in the pixel row. Accordingly, the detection result in the pixel row may be ignored, and the position of the trabecula in the whole ACA image may be specified (detected) based on the detection result in other pixel row.

Referring back to FIGS. 6 and 7, the drive control of the alignment mechanisms 5a and 5b will be continuously described.

First, the alignment in the XY-direction will be described.

For example, in a case where four ACA images captured at the positions of 0°, 90°, 180°, and 270° are obtained, the controller 80 performs the alignment in the X-direction (horizontal direction), based on two ACA images captured at the position of 0° and the position of 180°. More specifically, the controller 80 drives the alignment mechanisms 5a and 5b so that the positions of the trabecula in the radial direction (in this case, the horizontal direction) are substantially the same as each other (substantially symmetrical) between the ACA images captured at the position of 0° and the position of 180°. In this manner, the positional relationship in the X-direction (horizontal direction) is adjusted between the subject's eye E and the imaging optical system 30.

In addition, the controller 80 performs alignment in the Y-direction (upward/downward direction), based on the two ACA images captured at the position of 90° and the position of 270° among the four ACA images. More specifically, the controller 80 drives the alignment mechanisms 5a and 5b so that the positions of the trabecula in the radial direction (in this case, the vertical direction) are substantially the same as each other (substantially symmetrical) between the ACA images captured at the position of 90° and the position of 270°. In this manner, the positional relationship in the Y-direction (vertical direction) is adjusted between the subject's eye E and the imaging optical system 30.

Next, the alignment in the Z-direction will be described.

For example, as the operating distance (distance between the subject's eye E and the object reflection unit 50) is closer, the trabecula appears on the distal side from the fixation optical axis L1 in the ACA image. As the operating distance is farther, the trabecula appears on the fixation optical axis L1 side in the ACA image.

Therefore, for example, after the alignment is performed in the XY-direction, in the two ACA images captured at the imaging positions symmetrical with respect to the fixation optical axis L1, it is determined whether or not the trabecula in each ACA image is present at a predetermined target position in the ACA image. In this case, it is preferable that the target position is set to be located at substantially the middle of the ACA image.

Then, in a case where it is determined that the trabecula is present on the fixation optical axis L1 side from the target position, the alignment mechanism 5a is driven in the Z-direction in which the imaging optical system 30 moves close to the subject's eye E. On the other hand, in a case where it is determined that the trabecula is present on the distal side with respect to the fixation optical axis L1 from the target position, the alignment mechanism 5a is driven in the Z-direction in which the imaging optical system 30 moves away from the subject's eye E. In each case, the drive control of the alignment mechanism 5a may also be appropriately performed in the XY-direction.

However, without being necessarily circular, a case is conceivable where the entire periphery of the ACA is non-circular. Therefore, for example, in a state where the alignment in the Z-direction is properly performed based on the two ACA images captured at the position of 0° and the position of 180°, a case is conceivable where the operating distance is too short and/or too long in order to image the trabecula in the two ACA images captured at the position of 90° and the position of 270°. As a matter of course, a reversed case is also conceivable.

Therefore, for example, the position in the radial direction of the trabecula in the two ACA images captured at the position of 0° and the position of 180° and the position in the radial direction of the trabecula in the two ACA images captured at the position of 90° and the position of 270° may be averaged, and the alignment mechanism 5a may be driven in the Z-direction so that the averaged position is the target position.

In a case where the indicators 100 and 101 indicating the alignment state and the guide information 110 and 111 are displayed on the monitor 8, in FIG. 7, the alignment state in the XY-direction is indicated by the indicators 101 and 110 and the first guide information 110.

In addition, in FIG. 7, the alignment state in the Z-direction is indicated by indicators 100 and 101 and the second guide information 111.

In FIG. 7, the point-like indicator 100 superimposed on the ACA image indicates a detection position of the feature point (here, the trabecula) of the ACA. In addition, in FIG. 7, the rectangular reticle 101 indicates the alignment target position. In addition, the reticle 101 is an electronic indicator. In addition, as illustrated in FIG. 7, the target position may be set to have a proper margin. Based on whether or not the indicator 100 (feature point) is included in the target position (target region) indicated by the reticle 101, the alignment state in the X, Y, and Z directions can be recognized by the examiner.

However, the indicator 100 and the reticle 101 are dispersed on the four ACA images. Accordingly, it is difficult to simultaneously confirm the alignment state. It is conceivable that the unskilled examiner is less likely to intuitively recognize the alignment state. Therefore, in the present embodiment, the first and second guide information 110, 111 are further displayed. The first and second guide information 110 and 111 may be displayed in a sufficiently compact area compared to an area occupied by the four ACA images. For example, the first and second guide information 110 and 111 may be displayed in a space equal to or smaller than the area per one ACA image.

As illustrated in FIG. 7, in the present embodiment, the first and second guide information 110 and 111 are displayed in the middle of the plurality of ACA images displayed with the positional relationship corresponding to the imaging position. In this manner, the examiner is likely to observe each ACA image while the overall alignment state is recognized using the first and second guide information 110 and 111.

The first guide information 110 indicates the operation direction of the joystick 7 in a case where the alignment is manually adjusted. The circle at the center indicates the joystick. Concentric arc-shaped symbols appearing in the four directions of the upward, downward, rightward, and leftward directions indicate the operation amount of the joystick (in other words, the deviation amount of the alignment) required for the alignment target position.

The second guide information 111 is displayed adjacent to the first guide information 110. In FIG. 7, a wide line within a plurality of lines configuring the second guide information 111 indicates a proper position in the Z-direction. In accordance with a degree of alignment deviation in the Z-direction, a narrow line is added above and below the wide line. In a case where the apparatus is too close to the subject's eye E, the narrow line is displayed on the lower side. In a case where the apparatus is too far, the narrow line is displayed on the upper side.

In a case where the alignment state in the X, Y, and Z direction is the proper alignment state, a display mode of the indicators 100 and 101 and the guide information 110 and 111 may be switched. For example, the colors of the indicators 100 and 101 and the guide information 110 and 111 may be changed at the proper alignment state and the other states.

The alignment control in the XY-direction and the alignment control in the Z-direction as described above may be alternately repeated multiple times. In the present embodiment, in a case where it is determined that a predetermined alignment completion condition is satisfied, based on the ACA image, or in a case where an alignment completion signal is input by operating the operation unit 85, the process relating to the second alignment is completed (S14: Yes). In other cases, the process returns to S11, and the alignment operation is repeatedly performed (S14: No).

As a result of the above-described alignment operation (second alignment), the center in the entire periphery of the ACA of the subject's eye substantially coincides with the optical axis of the object reflection unit 50. In addition, when the optical deflection unit 48 is rotated so as to capture the ACA image at each imaging position in the entire periphery of the ACA, the trabecula is satisfactorily included in each ACA image.

Referring back to FIG. 5, the description will be continued. After the alignment is completed, the imaging operation is performed (S4).

In the present embodiment, as a result of the imaging operation, the ACA image focused on the trabecula is acquired as a captured image.

As an example, referring to FIG. 8, the imaging operation when the ACA image is continuously captured at 16 imaging positions obtained by dividing the entire periphery of the ACA into 16 pieces will be described.

The initial setting of the imaging position is performed (S21). For example, the imaging position of 0° may be predetermined as an initial position. The controller 80 drives and controls the driver 48*d* so that the initially set position is imaged. In this case, the driver 61*a* is driven so that the focus lens 61 is disposed in an end portion of the movable range.

In a case where the ACA image is captured at one imaging position, the controller 80 displaces the focus lens 61 in one direction from one end to the other end of the movable range. In this case, the controller 80 may determine the moving direction of the focus lens, depending on whether the focus lens is located in one end or the other end (S22 to S24). While the focus lens is moved, a plurality of ACA images are captured (S25). For example, the ACA images are captured at regular time intervals. As a result, the plurality of ACA images having mutually different focus states on the trabecula are obtained.

Next, the trabecula in each of the ACA images is detected (S26). The detection method may be the same as that in the second alignment. Then, a region including the trabecula which is the neighboring region of the trabecula is set in each of the ACA images (S27). A size and a shape of the neighboring region may be predetermined. For example, in the present embodiment, as illustrated in FIG. 8, the neighboring region having a rectangular shape is set.

Next, the controller 80 obtains evaluation information of the focus state on the trabecula for each image (S27). First, contrast (an example of the evaluation information of the focus state) in the neighboring region is obtained based on the luminance distribution in the neighboring region. Within the plurality of ACA images, an image most suitably focused on the trabecula is considered to be an image having the highest contrast in the neighboring region. Therefore, the ACA image having the highest contrast in the neighboring region is selected as a captured image (S28). The selected ACA image is stored in the memory 81, for example.

Thereafter, in a case where imaging positions which are not yet captured remain within 16 imaging positions (S29: Yes), the controller 80 rotates the optical deflection unit 48 as large as a predetermined angle (S30). The same imaging operation is performed at the subsequent imaging position (S22 to S28). When the plurality of ACA images are captured at a new imaging position, the controller 80 drives the focus lens 61 in the direction opposite to the immediately previous imaging position. In this way, in the present embodiment, in a case of continuously capturing the ACA images at two mutually different imaging positions, at the first imaging position, the controller 80 captures the plurality of ACA images while moving the focus lens 61 in one direction within a predetermined range. At the second imaging position where the ACA images are continuously captured, the controller 80 captures the plurality of ACA images while moving the focus lens 61 in the direction opposite to one direction. In this manner, in a case of continuously imaging the plurality of portions, the imaging time can be shortened.

Figure 9:
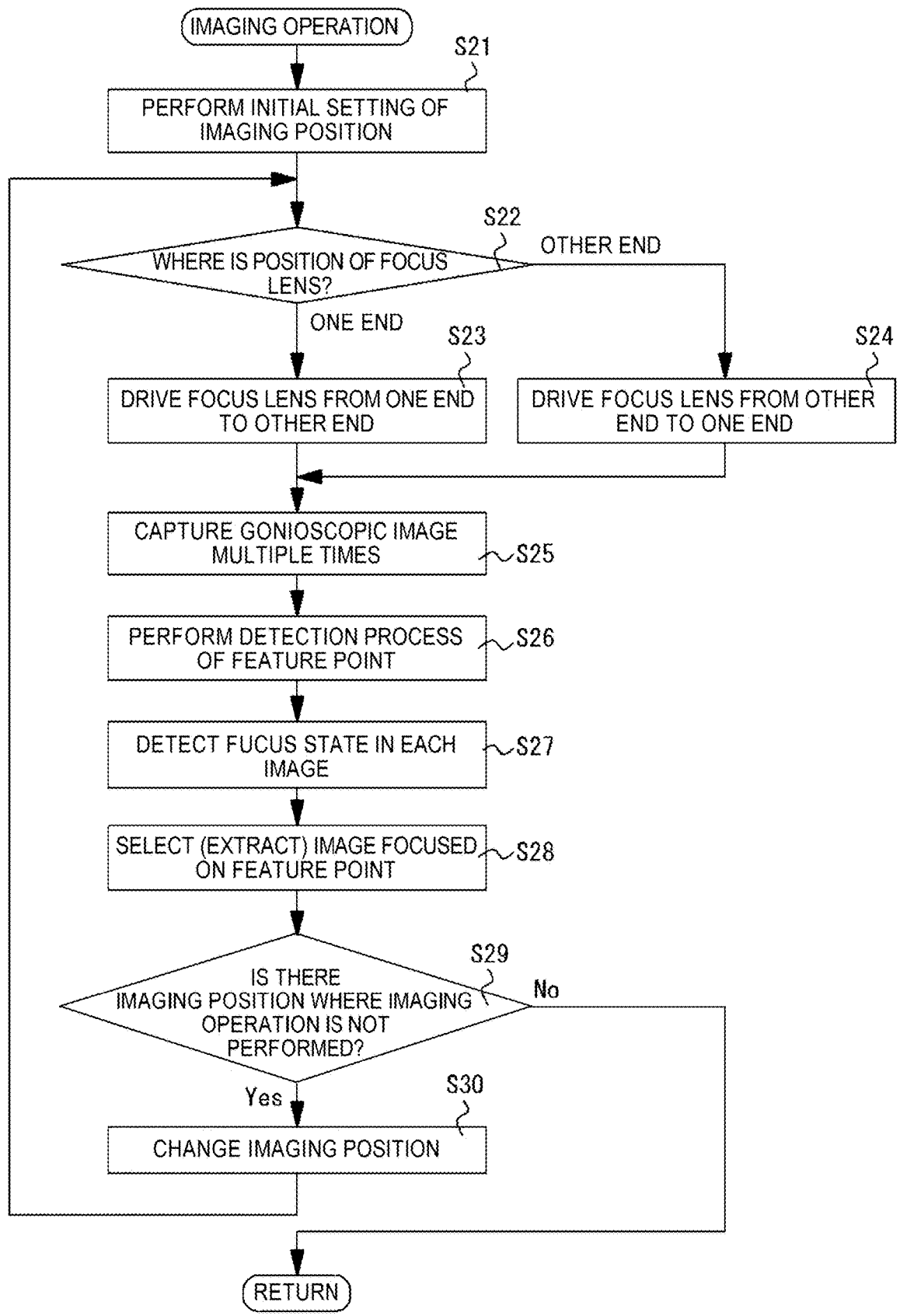
FIG. 9 is a flowchart illustrating an imaging operation.

The imaging position is switched so as to repeat the imaging operation. If the imaging operation is completed for all of the imaging positions (S29: No), the imaging operation illustrated in FIG. 9 is completed. As a result of performing the imaging operation on each imaging position, the plurality (here, 16) of ACA images focused on the trabecula at each imaging position can be obtained (as the captured image).

Figure 10:
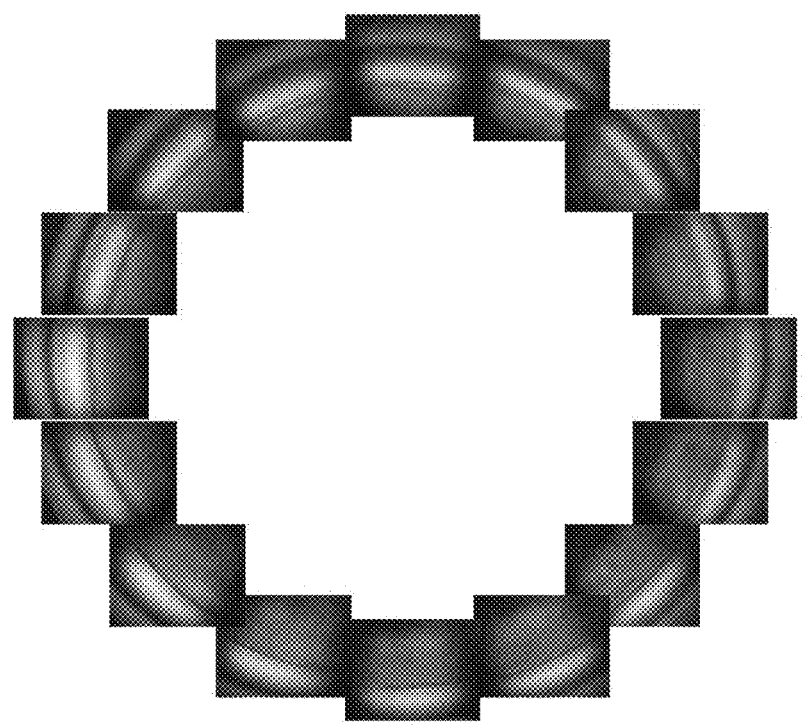
FIG. 10 is a view illustrating a display mode of an ACA image.

The controller 80 may cause the monitor 8 to display the ACA image captured in this way (S5). In this case, the 16 ACA images may be displayed side by side by using the layout illustrated in FIG. 10. That is, while the respective ACA images are associated with the positions of the imaging portion, the ACA images are disposed side by side in an annular shape. In this manner, the examiner can easily confirm a state of the trabecula in the entire periphery of the ACA.

As a matter Of course, the ACA images captured at the respective imaging positions need not be simultaneously displayed, and an image of any imaging position may be selectively displayed on the monitor.

Modification Example

Hitherto, the present disclosure has been described with reference to the embodiment. However, the present disclosure is not limited to the above-described embodiment, and various modifications can be made.

For example, in the second alignment according to the above-described embodiment, the controller 80 automatically drives and controls the alignment mechanisms 5*a* and 5*b*. However, the present disclosure is not limited thereto, and the alignment may be manually adjusted, based on the operation unit 85 or the joystick 7 operated by the examiner. In this case, the indicators indicating the alignment state as illustrated in FIG. 7 may be displayed on the monitor 8. In this case, the indicators represent one type of information (that is, guide information) for guiding the operation of the operation unit based on the position of the feature point in the ACA image.

In addition, any one of the manual alignment and the automatic alignment may be selectable. In this case, the alignment method (automatic or manual) may be selected in advance before the alignment based on the operation of the operation unit. In addition, during the alignment, the alignment method may be switched based on a predetermined operation.

In addition, for example, in the above embodiment, the plurality of ACA images having the mutually different focus states are respectively captured at the plurality of imaging positions. Therefore, a large amount of the ACA images is acquired by performing the imaging operation on each patient. Within the large amount of the acquired ACA images, in order to select at least the ACA image to be stored in the memory or in order to confirm the imaging position which needs the imaging operation again, a confirmation screen illustrated in FIG. 11 may be displayed on the monitor 8. For example, in the flowchart in FIG. 9, if the imaging operation is completely performed on all of the imaging positions (S29: No), the controller 80 may activate and display the confirmation screen.

The confirmation screen in FIG. 9 is roughly divided into three areas such as an enlarged display area 200, a first selection area 210, and a second selection area 220.

The first selection area 210 is provided in order to select the imaging position of the image to be displayed in the enlarged display area 200 and the second selection area 220.

Thumbnails of the ACA image representing each of the imaging positions are arrayed side by side in the first selection area 210. In this case, the thumbnails may be arrayed side by side in association with the imaging positions (for example, sequentially from a certain position in the clockwise direction).

Figure 11:
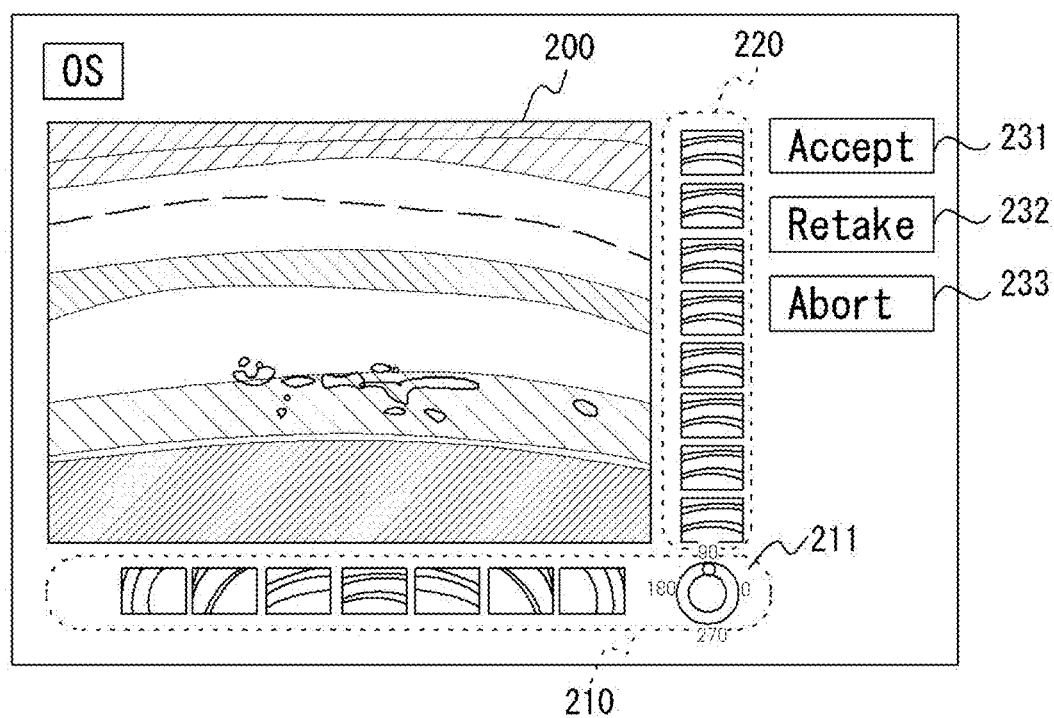
FIG. 11 is a view illustrating a display mode of a selection screen.

In the confirmation screen in FIG. 11, a widget 211 displayed in the first selection area 210 may be provided in order to select the imaging position by using a method other than the thumbnails. Alternatively, for convenience of space, in a case where the thumbnails corresponding to all of the imaging positions cannot be displayed in the first selection area 210, the widget 211 may be used for switching the thumbnails displayed in the first selection area 210.

In the enlarged display area 200, in the example illustrated in FIG. 11, the thumbnails of the ACA image are displayed side by side and one by one for each imaging position. Any one of the thumbnails is selected using a pointing device (an example of the operation unit). Then, other images captured at the same imaging position as that of the selected thumbnail are arrayed side by side in the second selection area 220. The images displayed in the second selection area 220 may also be the thumbnails. The thumbnails displayed in the second selection area 220 may be arrayed side by side in association with the focus when the ACA image corresponding to each thumbnail is captured. In this manner, it becomes easier to select the ACA image in a desired focus state from the thumbnails displayed in the second selection area 220.

In the enlarged display area 200, any one is displayed within the plurality of ACA images captured at the imaging positions corresponding to the thumbnails displayed in the second selection area 220. Any one of the thumbnails is selected in the second selection area 220, thereby switching the ACA image displayed in the enlarged display area 200 to the ACA image corresponding to the selected thumbnail.

In the confirmation screen illustrated in FIG. 11, three widgets 231 to 233 are further displayed. That is, three of an "Accept" button 231, a "Retake" button 232, and an "Abort" button 233 are displayed.

The "Accept" button 231 is used for selecting the image to be stored in the memory. In a case where the "Accept" button 231 is operated, the ACA image displayed in the enlarged display area 200 is displayed in the memory. Alternatively, the ACA images corresponding to the plurality of thumbnails displayed in the second selection area 220 may be entirely or partially stored in the memory. A configuration may be adopted in which any ACA image to be stored can be set in advance.

The "Retake" button 232 is used for performing the imaging operation again. In a case where the "Retake" button 232 is selected, the controller 80 performs the imaging operation again at the imaging positions (that is, the imaging positions selected in the first selection area 210) corresponding to the ACA images displayed in the enlarged display area 200. After the imaging operation is performed again, in a state where the imaging positions for performing the imaging operation again are selected in advance, the confirmation screen illustrated in FIG. 11 may be activated again. In this manner, it is possible to immediately confirm the result of the imaging operation performed again.

The "Abort" button 233 is used for deleting the ACA image captured at the selected imaging position. The "Abort" button 233 may be operated so as to delete all of the ACA images captured at the selected imaging position. In addition, the ACA images may be deleted little by little.

As a result of selecting the ACA image via the above-described confirmation screen, it is possible to satisfactorily reduce possibilities that unsuitable ACA images may be stored and displayed.

What is claimed is:

1. An ophthalmic apparatus comprising:
    an imaging optical system that includes a light projecting optical system for that projects light to an ACA region of an eye of a subject, and a light receiving optical system including a light receiving element that receives reflected light from the ACA region, and the imaging optical system has an imaging optical axis that is tilted relative to a fixation optical axis and that faces an ACA of the eye of the subject;
    an alignment driver configured to change a positional relationship between the eye of the subject and the imaging optical system;
    an imaging processor configured to generate an ACA image based on a signal output from the light receiving element; and
    a controller configured to detect a feature point in the ACA of the eye of the subject from the ACA image, and adjust the positional relationship in accordance with a position of the feature point in the ACA image, which is a position in a radial direction around the fixation optical axis.

2. The ophthalmic apparatus according to claim 1, wherein the controller drives and controls the alignment driver based on information relating to the position of the feature point in the ACA image.

3. The ophthalmic apparatus according to claim 1, wherein:
    the alignment driver changes the positional relationship between the eye of the subject and the imaging optical system based on an operation of an operation unit, and
    the controller outputs information that guides the operation of the operation unit based on information relating to the position of the feature point in the ACA image.

4. The ophthalmic apparatus according to claim 1, further comprising a switch configured to displace an orientation of the imaging optical axis relative to the fixation optical axis to capture the ACA image by the imaging optical system at two or more imaging positions having mutually different radial directions,
    wherein the controller adjusts the positional relationship such that the feature points are disposed at a same position in the radial direction in two or more ACA images captured at the mutually different imaging positions.

5. The ophthalmic apparatus according to claim 1, wherein the controller detects a trabecula as the feature point.

6. The ophthalmic apparatus according to claim 1, wherein:
    the ACA image is a color image, and
    the controller detects the feature point by performing a detection process depending on a color of an iris in the eye of the subject.

7. The ophthalmic apparatus according to claim 6, wherein the controller is configured to acquire information relating to the color of the iris in the eye of the subject.

8. The ophthalmic apparatus according to claim 7, wherein the controller acquires the information relating to the color of the iris based on the ACA image.

9. The ophthalmic apparatus according to claim 1, wherein:

the imaging optical system includes an objective optical system that bends light emitted from a light source to tilt an imaging optical axis relative to a fixation optical axis and to guide the emitted light to the ACA region of the eye of the subject, and illumination light is emitted to a tissue surface of the ACA region via the objective optical system, and reflected light from the tissue surface is received by the light receiving element.

10. An ophthalmic apparatus comprising:
an imaging optical system that includes a light projecting optical system that projects light to an ACA region of an eye of the subject, and a light receiving optical system including a light receiving element that receives reflected light from the ACA region;
a focus changing device configured to drive a portion of the imaging optical system to change a focus state of the reflected light in the light receiving element;
an imaging processor configured to generate an ACA image based on a signal output from the light receiving element; and
an image processing unit configured to obtain evaluation information of the focus state based on image information of the ACA image, and acquire, as the evaluation information, information relating to contrast in a neighboring region of a feature point in an ACA of the eye of the subject, which includes the feature point.

11. The ophthalmic apparatus according to claim 10, wherein the image processing unit detects the feature point in an ACA of the eye of the subject from the ACA image, and obtains the evaluation information of the focus state based on the image information relating to the feature point.

12. The ophthalmic apparatus according to claim 10, further comprising a controller configured to drive the focus changing device to change the focus state, and capture a plurality of ACA images having mutually different focus states, wherein:
the image processing unit acquires the evaluation information for each of the plurality of ACA images having the mutually different focus states, and
the image processing unit selects the ACA image focused on the feature point from the plurality of ACA images based on the evaluation information of the respective plurality of ACA images.

13. The ophthalmic apparatus according to claim 12, further comprising a switch configured to displace an imaging position of the imaging optical system with respect to an entire periphery of the ACA, wherein:
the focus changing device changes the focus state by moving a focus lens within a predetermined range along an optical path of the imaging optical system,
when the controller continuously captures the ACA images at mutually different imaging positions, the controller captures the plurality of ACA images at a first imaging position while moving the focus lens in one direction within the predetermined range, and
the controller captures the plurality of ACA images at a second imaging position while moving the focus lens in a direction opposite to one direction.

14. The ophthalmic apparatus according to claim 10, further a controller that controls the focus changing device so as to be focused on the feature point based on the evaluation information.

15. The ophthalmic apparatus according to claim 14, wherein:
the controller (i) drives the focus changing device to change the focus state, (ii) captures the plurality of ACA images having the mutually different focus states, and (iii) causes the image processing unit to acquire the evaluation information for each of the plurality of ACA images, and
the controller drives the focus changing device such that the images selected from the plurality of ACA images by the image processing unit have the same focus state.

16. The ophthalmic apparatus according to claim 10, further comprising a switch configured to displace an imaging position of the imaging optical system with respect to an entire periphery of the ACA,
wherein a controller causes the switch to switch the imaging positions, and controls the focus state at the plurality of mutually different imaging positions.

17. The ophthalmic apparatus according to claim 10, further comprising an imaging optical system that includes an objective optical system that bends light emitted from a light source to tilt an imaging optical axis relative to a fixation optical axis and that guides the emitted light to the ACA region of the eye of the subject, and includes a light receiving element configured to emit illumination light to a tissue surface of the ACA region via the objective optical system and to receive reflected light from the tissue surface.

* * * * *